United States Patent [19]

Drake

[11] Patent Number: 6,060,461
[45] Date of Patent: May 9, 2000

[54] TOPICALLY APPLIED CLOTTING MATERIAL

[76] Inventor: James Franklin Drake, 901 20th Ave. SE., Minneapolis, Minn. 55414

[21] Appl. No.: 09/246,231

[22] Filed: Feb. 8, 1999

[51] Int. Cl.[7] ................................................. A61K 31/715
[52] U.S. Cl. ................................ 514/54; 514/57; 514/58; 514/60
[58] Field of Search ................................ 514/54, 57, 58, 514/60

[56] References Cited

U.S. PATENT DOCUMENTS

| | | | |
|---|---|---|---|
| 4,188,390 | 2/1980 | Campbell | 424/251 |
| 4,317,729 | 3/1982 | Yamashita et al. | 210/500.2 |
| 4,344,949 | 8/1982 | Hoefle et al. | 424/258 |
| 4,373,519 | 2/1983 | Errede et al. | 128/156 |
| 4,482,514 | 11/1984 | Schindler et al. | 264/41 |
| 4,740,594 | 4/1988 | Mauzac et al. | 536/57 |
| 4,743,450 | 5/1988 | Harris et al. | 424/440 |
| 5,348,941 | 9/1994 | Middaugh et al. | 514/12 |
| 5,529,929 | 6/1996 | Rossi, Jr. et al. | 435/280 |
| 5,593,729 | 1/1997 | Frechet et al. | 427/337 |
| 5,624,612 | 4/1997 | Sewall et al. | 264/4.1 |
| 5,675,006 | 10/1997 | Karimian et al. | 544/283 |
| 5,686,612 | 11/1997 | Karimian et al. | 544/284 |
| 5,700,902 | 12/1997 | Hancock et al. | 528/373 |
| 5,817,381 | 10/1998 | Chen et al. | 428/34.8 |

OTHER PUBLICATIONS

Associated Press, "FDA approves glue to replace some stitches", *The Augusta Chronicle*, http://augustachronicle.com/stories/082898/tec_124–8747.shtml.BAK1, 1–2, (Aug. 27, 1998).

Dr. Christopher, "Abrasions", *Dr. Christopher Enterprises*, http://www.drchristopher.com/ail/abrasio3.htm, 1–2, (1998).

Encyclopedia, "Anticoagulant", *The Columbia Encyclopedia, Fifth Edition, Columbia University Press*, http://www.infoplease.com/ce5/CE002395.html, 1, (1993).

McCall, W., "Lasers, elastin patch could stem bleeding on battlefields", *The Detroit News*, http://detnews.com/96/discover/9701/05/12300058/htm, 1–2, (Dec. 30, 1996).

Merritt, T.B., "Help!My Bird is Bleeding", *Winged Wisdom Pet Bird Magazine, Ezine*, Article V http://www.birdsnways.com/wisdom/ww17ev.htm, 1–2, Nov. 1997).

Thermogenesis, "Asahi Medical to Begin Initial Human Clinical Studies in Japan of the ThermoGenesis CryoSeal System Pre–Clinical Study Validates Clotting Adhesive and Wound–Healing Protein Levels in Cryoprecipated AHF Produced by CryoSeal System", ThermoGenesis Press Release, http://www.thermogenesis.com/pressreleases/preclinic.html, 1–2, (Aug. 1997).

Warkentin, T.E., "Recent Advancements in the Mangement of Heparin–Induced Thrombocytopenia", *Thrombosite Nwsletter, vol. 1,* Iss. 1, http://www.thrombosite.com/tsnews/tsnews1_1.html, 1–16, (Mar. 1998).

*Primary Examiner*—Gary L. Kunz
*Assistant Examiner*—Everett White
*Attorney, Agent, or Firm*—Schwegman, Lundberg, Woessner & Kluth P.A.

[57] ABSTRACT

A composition, system, articles and method for the enhancement of clotting in wounds with extravascular blood flow, especially where the surface of the tissue has been broken is described. The system consists of biotolerable, porous particulates applied to the surface of a wound with liquid blood thereon. The porous nature of the particulate material, either free-flowing or packaged or restrained on or in a surface, enhances clotting. Chemical or biochemical agents, such as additional clotting agents, therapeutic agents, antibiotics, clot strengthening agents (such as fibrous structural materials), and the like may optionally be included on, with or within the porous particles. The particles may comprise such diverse materials as organics, metallics, inorganics, ceramics, and the like, both natural and artificial. It is generally preferred that the pore size distribution lies within a general range, and this range may vary from animal to animal and condition to condition, but generally falls within about 0.5 to 1000 nanometers or 3,000 to 200,000 Daltons.

31 Claims, No Drawings

TOPICALLY APPLIED CLOTTING MATERIAL

BACKGROUND OF THE INVENTION

1. Field of the Invention

The present invention relates to the field of topical application to tissue (both internal tissue and external tissue) for the reduction of bleeding, especially by the formation of clots on the surface, exposed areas, and opened area from wounds.

2. Background of the Art

External wounds and concomitant bleeding arc the most common injuries suffered by animals. Scratches, cuts, abrasions, lacerations, punctures and other categories or breakage of layers of tissue, especially skin, each act to cause breakage of protective tissue and blood vessels, allowing blood to flow out of its normal passageways. Bleeding provides a first line defense against damage from the ancillary effects of the trauma that caused the injury. The flow of blood washes material out of the wound and the blood clots to seal the wound area. The types of materials washed from the wound by the flow of blood from the traumatized area includes material introduced into the wound area by any foreign object which caused the wound (including biological species such as bacteria and viruses and inorganic species such as particulates). The clotting prevent migration of materials into the wound area, and therefore into the animals body, thus reducing the likelihood of subsequent infection of the wound, even after materials originally introduced into the wound have been removed or reduced in volume by the initial blood flow.

Clotting is essential to both the short term and long term process of healing the wound. In the short term, after the wound has been partially cleansed by blood flow, the clotting entraps these removed materials so that they will not easily reenter the wound and stops the blood flow so that excessive blood loss will not occur. In the long term, the clot secures the wound so that additional tissue trauma (e.g., from flexing of the area) is reduced and reduces the ability of biological materials from entering the wound and entering the blood stream to cause infection.

Clotting is a complex biological process, and is categorized as one of the cascading processes in which series of organic/biological chemical reactions must occur in a specific sequence to cause the final effect of protected the wound. In lay terms, the events in a simple wound where blood flow has occurred can be described as following a reaction path where a) Blood cells leak into a wound area b) Blood vessels usually contract in the wound area to reduce the flow of blood c) Platelets in the blood aggregate and adhere to tissue at the damaged site, even plugging small blood vessels d) Platelets also interact with collagen, phospholipids, and tissue factor (a lipid-containing protein or lipoprotein, that stimulates blood clot formation)

e) The platelets break-up and release thromboplastin, a poorly defined mixture of phospholipids and proteins that activate a series or cascade of reactions, usually catalyzed by serine proteases f) The platelets provide nuclei upon which fibrin is bound to form the first stage of the moist clot, followed by subsequent maturation of the clot to form a firm coherent mass g) Tissue forming cells, fibroblasts, approach the wound and associate with the moist clot to strengthen the region h) The clot dehydrates, usually through evaporative processes, although there may be some absorption of liquid into the tissue I) Phagocytes (white blood cells) move into the wound area to ingest microorganisms, cellular debris and any residual foreign matter j) Epidermal cells at the edge of the wound divide and build a bridge across the wound.

The actual chemical and biological processes involved in the clotting process are quite complex and sophisticated. The process must be very selective, forming clots under only exacting conditions, so that clot formation does not occur in the circulatory system where clotting would itself be dangerous, causing phlebitis and certain types of strokes.

Wound management and clotting enhancement for wounds has taken many different paths over the years. There are a wide variety of different methodologies available for the management of wounds, depending, at least in part upon the type of wound and its severity. The two most common and effective treatments for minor bleeding wound management, following cleansing of the wound area, include direct application of pressure to the wound area and the topical application of an absorptive bandage to the wound surface. To assure the reduction of direct or secondary infections, all wound management should include cleansing and application of an antimicrobial agent to the wound area. After this cleansing step, the other methods may follow. Direct application of pressure is usually effected by application of pressure manually or with a light wrapping. A sterile article is placed over the wound and pressure applied to the wound through the sterile article (e.g., a fabric, such as gauze, cotton ball, bandage, or other available, preferably sterilized or at least cleaned fabric). The pressure acts to assist in closing blood vessels in the area to reduce blood flow, absorb some of the initial blood flow with the highest content of foreign matter carried therein, and to stabilize the movement of the blood so that clotting is give time to initiate. The application of bandages to the wound area primarily acts to absorb excess blood, flow, provide a longer term barrier over the wound against introduction of foreign agents, protect the clot while it is still fragile (allowing it to dehydrate in the first twenty-four hours), and possibly carry and retain antimicrobial material to the wound surface.

The use of lasers, alone or in combination with topically applied patch materials (e.g., an elastin patch made from animal tissue), has been suggested for field treatment of bleeding wounds, both internal wounds and external or topical wounds. This has been specifically suggested as a field treatment, especially for the military, police, fire, and rescue services. Lasers by themselves can cauterize and seal vessel and organ wounds, and the patch can provide additional structural support for the area. Http://detnews.com/96/discover/9701/05/12300058.htm.

Many folk remedies have also been applied as abrasion, but not open wound, treatments. For example, www://.drchristopher.com/ail/abrasio3.htm suggests the use of specific natural material treatments for abrasions where the skin has not been broken. The natural herbal agents include wheat grass chlorophyll, comfrey, healing ointment (comfrey, marshmallow, marigold, beeswax and oils), myrrh, plantain (and banana is also well known), and cayenne pepper. These materials may be applied directly to the abrasion area or carried on another surface, often with wetting suggested to retain the herbal abrasion treatment material. An Asian home remedy includes Dit Da Jao ("Iron Wine) which is a tincture remedy applied to relieve pain, stimulate blood flow and chi flow, and break up clots and bruises. The tincture is made up from powdered herbs and alcohol, with strained herbal residue discarded and the liquid tincture applied to the wound surface. The herbs to be used include Arnica blossom, comfrey, blessed thistle, goldenseal root, ginger root, Myrrh, sasparilla root, and witch hazel. (Http://ww.aikidofaq.com/n_section51.html)

Newer technology for wound management is the use of chemical bandages, or literally polymeric film-forming material over the wound area. This technology has passed from a fairly unsophisticated application of liquid glues (e.g., cyanoacrylate adhesives, gelatinous glues, and UV curable polymers) to the wound surface. In 1998, only the second liquid glue was granted FDA approval for use as stitches in addition to clotting enhancement, the glue apparently comprising a formaldehyde content cyanoacrylate. This glue is Closure Medical Corporation's DermaBond™, which is used as an alternative to Baxter HealthCare Corporation's Tisseel™, which is made from two blood proteins that naturally cause blood to clot. The cyanoacrylate must have a strong tendency for tissue irritation and carries a standard recommendation against use with patients with sensitivities to acrylates and formaldehyde, which are fairly common. HealthCare Corporation's Tisseel™, which is made from specific blood proteins is relatively expensive to manufacture. In addition, the use of human or animal derived protein compositions carries the risk of contamination by infectious agents such as hepatitus viruses, Human Immuno-Deficiency (HIV) viruses, or prions such as have been related to mad cow disease (bovine spongiform encephalitis) and Jacob-Kreutzer disease. The Cryoseal™ clotting system is a cryoprecititated adhesive with wound-healing proteins present in cryoprecititated AHF. This is suggested for use in a floor-standing thermodynamic device in an operating theater, for example, as a wound closure system including the fibrin glue.

It is always desirable to find alternative solutions to wound management problems.

SUMMARY OF THE INVENTION

A composition, system, articles and method for the enhancement of clotting in wounds with extravascular blood flow, especially where the surface of the tissue has been broken is described. The system consists of biotolerable, porous particulates (with pores chosen of the appropriate size for the effect desired) applied to the surface of a wound with liquid blood thereon. The porous nature of the particulate material, either free-flowing or packaged or restrained on or in a surface, enhances clotting. Chemical or biochemical agents, such as additional clotting agents, therapeutic agents, antibiotics, clot strengthening agents (such as fibrous structural materials), and the like may optionally be included on, with or within the porous particles. Where the porous particle clotting agent are used with animals, materials which are mildly repellant to the animal patient (without being toxic) may be included within the applied particle material to assure that the animal will not tamper with the wound during healing, a common problem with veterinary treatments. The particles may comprise such diverse materials as organics, metallics, inorganics, ceramics, and the like, both natural and artificial. It is generally preferred that the pore size distribution lies within a general range, and this range may vary from animal to animal and condition to condition, but generally falls within about 0.5–1000 nm or 1 to 1000 nm, or about 5 to 500 nm, depending upon the particular use.

DETAILED DESCRIPTION OF THE INVENTION

A composition which may be used for the enhancement of the clotting of blood in animals, including mammals, avians and reptiles comprises porous particulate material which is applied to the wound when there is blood in a liquid or only partially clotted state (e.g., where it may wet the particles). The particles may be applied to the wound area either as a free flowing powder of the particles, a dry spray of particles, a moist spray or aerosol of the particles, as an association of particles in or on a carrier (such as a web, tape, fabric, foam, reticulated foam, or film), and may optionally contain conventional clotting agents with the particles. The particle application should enable direct contact of the particles with the flow of blood, preferably without any non-clotting intermediate film or material between the blood at the site of the wound and the clotting particles. For example, the use of the particles on the surface of a film with that surface facing the wound would be acceptible. In that orientation, the blood would clot on the wound site. On the other hand, where a fairly thick, but porous film was used, and the blood flowed through the pores of the film (e.g., greater than 0.1 mm thickness) to reach the porous clotting particles on a backside of the film, the clot would not occur on the wound site. That would not be the most advantageous location for the clot enhancing particles. An intermediate and acceptable structure would be to have the particles located within a thin, light fibrous mass so that as the particles enhanced clotting, the fibers would remain within the region of clotting and strengthen the clot. The fibers could also be used to assist in carrying optional materials (e.g., antibiotics) to the wound site. One type of desirable materials of this last format would have a woven, non-woven or knitted fibrous sheet (e.g., less than 1 mm in thickness, e.g., 0.05 to 0.5 mm, or 0.1 to 0.5 mm thick) with the fabric having a porosity of at least 30% (e.g., 30–95%, 40–95%, or 50–95% porosity), with at least a portion of the porosity filled with the clot enhancing particles described for use in the practice of the present invention. The particles may be carried within the structure of the fabric or bonded to the fibers, filaments, or yarns of the fibrous material (taking care not to completely fill the pores of the particles with any binder used).

The particles may generally have a size of from about 1 to 1000 micrometers, or 1 to 500 micrometers, but the size may be varied by one ordinarily skilled in the art to suit a particular use or type of patient and depending on the ability of a carrier to support the particles with their optional selection of sizes. Examples of specific materials useful in the practice of the present invention comprise porous materials from within the classes of polysaccharides, cellulosics, polymers (natural and synthetic), inorganic oxides, ceramics, zeolites, glasses, metals, and composites. Preferred materials are of course non-toxic and are provided as a sterile supply. The polysaccharides are preferred because of their ready availability and modest cost. The porous particulate polysaccharides may be provided as starch, cellulose and/or pectins, and even chitin may be used (animal sourced from shrimp, crab and lobster, for example). Glycosaccharides or glycoconjugates which are described as associations of the saccharides with either proteins (forming glycoproteins, especially glycolectins) or with a lipid (glycolipid) are also useful. These glycoconjugates appear as oligomeric glycoproteins in cellular membranes. In any event, all of the useful materials must be porous enough to allow blood liquid and low molecular weight blood components to be adsorbed onto the surface and/or absorbed into the surface of the particles. Porosity through the entire particle is often more easily achieved rather than merely etching the surface or roughening the surface of the particles.

Ceramic materials may be provided from the sintering, or sol-gel condensation or dehydration of colloidal dispersions of inorganic oxides such as silica, titanium dioxide, zirconium oxide, zinc oxide, tin oxide, iron oxide, cesium oxide, aluminum oxide and oxides of other metal, alkaline earth, transition, or semimetallic chemical elements, and mixtures thereof. By selection of the initial dispersion size or sol size of the inorganic oxide particles, the rate of dehydration, the temperature at which the dehydration occurs, the shear rate within the composition, and the duration of the dehydration, the porosity of the particles and their size can be readily controlled according the skill of the ordinary artisan.

With regard to cellulosic particles, the natural celluloses or synthetic celluloses (including cellulose acetate, cellulose butyrate, cellulose propionate, etc.) may be exploded or expanded according to techniques described in U.S. Pat. No. 5,817,381 and other cellulose composition treating methods described therein which can provide porous particles, fibers and microfibers of cellulose based materials. Where the porous materials, whether of cellulose or other compositions, have a size which may be too large for a particular application, the particles may be ground or milled to an appropriate size. This can be done by direct mortar and pestle milling, ball milling, crushing (as long as the forces do not compress out all of the porosity), fluidized bed deaggregation and size reduction, and any other available physical process. Where the size of the raw material should be larger than the particle size provided, the smaller particles may be aggregated or bound together under controlled shear conditions with a binder or adhesive until the average particle size is within the desired range.

Porosity may be added to many materials by known manufacturing techniques, such as 1) codispersion with a differentially soluble material, and subsequent dissolution of the more soluble material, 2) particle formation from an emulsion or dispersion, with the liquid component being evaporated or otherwise removed from the solid particle after formation, 3) sintering of particles so as to leave porosity between the sintered or fused particles, 4) binding particles with a slowly soluble binder and partially removing a controlled amount of the binder, 5) providing particles with a two component, two phase system where one component is more readily removed than another solid component (as by thermal degradation, solubilization, decomposition, chemical reaction such as, chemical oxidation, aerial oxidation, chemical decomposition, etc.), and other known process for generating porosity from different or specific types of compositions and materials. Where only surface porosity is needed in a particular clot promoting format, surface etching or abrasion may be sufficient to provide the desired surface porosity.

A particularly desirable and commercially available material comprises polysaccharide beads, such as dextran beads which are available as Sephadex™ beads from Pharmacia Labs. These are normally used in surgery as an aid to debridement of surfaces to help in the removal of damaged tissue and scar tissue from closed wounds. The application of this type of porous bead (and the other types of porous beads to open wounds with blood thereon) has been found to promote hemostasis, speeding up the formation of clots, and reducing blood loss and the need for continuous cleaning of the wound area. Bleeding from arteries, veins and small capillaries, soft tissue, organs (e.g., liver, kidney, lungs and spleen) can be effectively managed, reduced and eliminated in most cases by application of the particles or beads according to the present invention.

The porous particles or porous beads may be directly applied to surfaces or held in place by pressure. The beads or particles may be free flowing or be supported on or in a containment system. For example, the particles may be adhered to the surface of a sheet or film which is applied (e.g., contacted, wrapped, adhered, secured, affixed or otherwise place into a position where blood on the wound area will be absorbed or adsorbed by the porous particles or porous beads) to areas of a wound with blood thereon. The particles may also be provided in a form where the porous particles or porous beads may be interspersed with fibers, filaments or other particles in a self-supporting structure, entangled within the fibrous elements of a net, web, fabric or sheet, embedded in a sheet or film (with the particles exposed to enable adsorption or absorption of blood in contact with the wound), a packet of material, with the particles or beads free-flowing within the confines of the packet. The terms particles and beads are not intended to denote any substantive difference in size, shape or performance of materials and are not asserted as having any distinct differences within the practice of the present invention, but are merely alternative terms. The use of only one term does not intend that the other term is not equally applicable in the context in which the one term is used. The porous particles and porous beads may also be provided as part of a patch system, with a fibrous network associated with the particles to provide a high level of structural integrity and strength to the applied assembly over the wound, even before clotting has occurred. This would be particularly appropriate where the assembly was being used as a stitch replacement or true wound closure system rather than only promoting clotting.

The porous particles may easily be associated with or carry additional, but optional, clotting or wound treating materials or ingredients. For example, it would be desirable to provide the porous particles with antibiotics, antifungal agents (especially where application may be in a tropical environment), topical pain reducing medication, pharmaceuticals, anti-inflammatants, tissue enzyme inhibitors (e.g., epsilon aminocaproic acid, to reduce tissue enzyme production that would weaken the blood clot), and the like. Existing materials which promote clotting or control bleeding would be particularly, such as thrombin, fibrinogen, aprotinin, fibronectin, and factor XIII. However, one of the advantages of the materials which may be used (excluding those derived from animals) is that they are not made from animal components as are the typical clotting or wound treatment materials noted above. As there is always a potential for animal based materials being a source of infection themselves (e.g., viral infection, spongiform encephalopathy, allergic reactions, etc.), the avoidance of animal based products, which can be easily accomplished in the practice of the present invention, is desirable.

The preferred polysaccharide components for the porous particles and porous beads of the present invention may often be made from cross-linked polysachharides, such as cross-linked dextran (poly[beta-1,6-anhydroglucose]). Dextran is a high molecular eight, water-soluble polysaccharide. It is not metabolized by humans, is non-toxic, and is well tolerated by tissue in most animals, including most humans. There have even been extensive use of solubilized dextrans as plasma substitutes. The Sephadex™ beads specifically mentioned in the description of particularly useful polysaccharides comprise dextran crosslinked with epichlorihydrin. These beads are available in a variety of bead sizes (e.g., 10 to 100 micrometers, with a range of pore size. It is believed that pore sizes on the order of from 5 to 75% of volume may be commercially available and can be expanded to from 5 to 85% by volume or manufactured with those properties from amongst the type of beads described above. The sizes of the pores may also be controlled to act as molecular sieves, the pore size being from 0.5% or 1 to 15% of the largest diameter of the particles or beads. The Sephaex™ beads are promoted as having controlled pore sizes for molecular weight cutoff of molecules during use as a sieve, e.g., with cutoff molecular being provided at different intervals between about 5,000 Daltons and 200,000 Daltons. For example, there are cutoff values specifically for molecular weight sizes of greater than 75,000 Daltons. This implies a particle size of specifically about 10 to 40 microns. These beads will rapidly absorb water, swelling to several times their original diameter and volume (e.g., from 1.2 to as much as five times their volume).

EXAMPLE

Surgery to remove the claws of domestic cats can result in considerable bleeding unless precautions are taken to prevent this complication. Generally, following removal of the claw at the first joint, the artery leading to the tip of the digit is sealed by suturing, application of surgical glues, or other available means. Despite these conventional treatments, considerable bleeding often follows removal of the claws, often requiring additional veterinary treatment. Application of cyanoacrylate-based adhesives to control such bleeding often results in inflammation and development of granulomatous deposits as a complication. The following examples show the usefulness of the practice of the present invention within the realm of cat declawing surgery.

A domestic cat was anesthetized and prepared for de-claw surgery in a standard manner. Preparation of the patient included the application of a tourniquet to prevent bleeding during the procedure. Following removal of the claw, the remaining cavity was filled with dry, free-flowing Sephadex™ G-25 powder (Pharmacia, Inc.), a cross-linked dextran bead having an average particle size of 20 to 80 micrometers, with a molecular weight size exclusion of 3,000 Daltons. The powder was applied to the cavity of the wound with a plastic dropper (e.g., eye dropper), the powder firmly pressed into the wound cavity, and firm pressure maintained on the powder in the wound cavity for about one minute. The efficacy of the procedure was tested by loosening the tourniquet and watching for any bleeding from the fresh wound. The procedure was repeated for each of the claws on each of the four feet of the cat. None of the wounds showed any significant blood loss. The attending veterinarian judged the procedure to be equal to or better than the use of surgical glue for controlling bleeding during the procedure. Following the surgery, the cat recovered normally, with no signs of inflammation or granulomatous lesions at the surgical site.

What is claimed:

1. A method for enhancing the formation of clots on a wound of an animal where blood is present comprising the steps of applying porous part dimensions of from about 0.5 to 1000 micrometers to at least a portion of said wound where blood is present in said wound, allowing said porous particles to remain in contact with said blood in said wound while clotting initiates in said wound.

2. The method of claim 1 wherein said animal is selected from the group consisting of mammals, avians, and reptiles.

3. The method of claim 2 wherein said porous particles have molecular sieve cutoff values between about 5,000 Daltons and 200,000 Daltons.

4. The method of claim 2 wherein said pores comprise from 5 to 75% b of the volume of the porous particles.

5. The method of claim 2 wherein said pores comprise from 5 to 35% of the volume of the porous particles.

6. The method of claim 2 wherein said particles are applied to a surface of said wound with blood as free-flowing particles.

7. The method of claim 2 wherein said particles are applied to a surface of said wound with blood with said particles associated with a fabric material.

8. The process of claim 2 wherein said porous particles are applied to said wound surface along with another material selected from the group consisting of antibiotics, antifungal agents, topical pain reducing medication, pharmaceuticals, anti-inflammatants, and tissue enzyme inhibitors.

9. The process of claim 2 wherein said porous particles are applied to said wound surface on a non-human mammal along with another material selected from the group consisting of antibiotics, antifungal agents, topical pain reducing medication, animal repellant, pharmaceuticals, anti-inflammatants, and tissue enzyme inhibitors.

10. The method of claim 1 wherein said animal is a human.

11. The method of claim 10 wherein the wound comprises broken skin tissue.

12. The method of claim 10 wherein the wound comprises broken soft tissue within a human body.

13. The method of claim 10 wherein said particles comprise a polysaccharide.

14. The method of claim 13 wherein said polysaccharide comprises dextran.

15. The method of claim 14 wherein said dextran is crosslinked.

16. The method of claim 15 wherein said porous particles have molecular sieve cutoff values between about 5,000 Daltons and 200,000 Daltons.

17. The method of claim 15 wherein said pores comprise from 5 to 35% of the volume of the porous particles.

18. The method of claim 14 wherein said pores comprise from 5 to 35% of the volume of the porous particles.

19. The method of claim 13 wherein said pores comprise from 5 to 35% of the volume of the porous particles.

20. The method of claim 13 wherein said particles are applied to a surface of said wound with blood with said particles associated with a fabric material.

21. The method of claim 1 wherein said particles comprise a polysaccharide.

22. The method of claim 1 wherein said pore size is between 1 and 500 nanometers.

23. A method for enhancing the formation of clots on a wound of an animal where blood is present comprising the steps of applying porous particles having average diameter dimensions of from about 0.5 to 1000 nanometers to at least a portion of said wound where blood is present, allowing said porous particles to remain in contact with said blood while clotting initiates.

24. A method for enhancing the formation of clots on a wound of an animal where blood is present comprising the steps of applying porous particles to blood in said wound without any non-clotting intermediate film or material between said particles and said blood, the particles having average diameter dimensions of from about 0.5 to 1000 micrometers to at least a portion of said wound where blood is present, allowing said porous particles to remain in contact with said blood while clotting initiates in said wound.

25. The method of claim 24 wherein said animal is a mammal.

26. The method of claim 25 wherein said particles comprise a polysaccharide.

27. The method of claim 6 wherein said polysaccharide comprises dextran.

28. The method of claim 27 wherein said dextran is crosslinked.

29. The method of claim 28 wherein said porous particles have molecular sieve cutoff values between about 5,000 Daltons and 200,000 Daltons.

30. The method of claim 29 wherein said pores comprise from 5 to 75% of the volume of the porous particles.

31. The method of claim 30 wherein said pores comprise from 5 to 35% of the volume of the porous particles.

* * * * *

(12) EX PARTE REEXAMINATION CERTIFICATE (9270th)
United States Patent
Drake

(10) Number: US 6,060,461 C1
(45) Certificate Issued: Sep. 4, 2012

(54) TOPICALLY APPLIED CLOTTING MATERIAL

(75) Inventor: James Franklin Drake, Minneapolis, MN (US)

(73) Assignee: Hemarrest, Inc., Edina, MN (US)

Reexamination Request:
No. 90/011,794, Jul. 13, 2011

Reexamination Certificate for:
Patent No.: 6,060,461
Issued: May 9, 2000
Appl. No.: 09/246,231
Filed: Feb. 8, 1999

(51) Int. Cl.
*A61K 31/715* (2006.01)
*A61K 31/716* (2006.01)
*A61K 31/721* (2006.01)

(52) U.S. Cl. .............................. 514/54; 514/57; 514/58; 514/60

(58) Field of Classification Search .................. None
See application file for complete search history.

(56) References Cited

To view the complete listing of prior art documents cited during the proceeding for Reexamination Control Number 90/011,794, please refer to the USPTO's public Patent Application Information Retrieval (PAIR) system under the Display References tab.

*Primary Examiner* — Johnny F Railey

(57) ABSTRACT

A composition, system, articles and method for the enhancement of clotting in wounds with extravascular blood flow, especially where the surface of the tissue has been broken is described. The system consists of biotolerable, porous particulates applied to the surface of a wound with liquid blood thereon. The porous nature of the particulate material, either free-flowing or packaged or restrained on or in a surface, enhances clotting. Chemical or biochemical agents, such as additional clotting agents, therapeutic agents, antibiotics, clot strengthening agents (such as fibrous structural materials), and the like may optionally be included on, with or within the porous particles. The particles may comprise such diverse materials as organics, metallics, inorganics, ceramics, and the like, both natural and artificial. It is generally preferred that the pore size distribution lies within a general range, and this range may vary from animal to animal and condition to condition, but generally falls within about 0.5 to 1000 nanometers or 3,000 to 200,000 Daltons.

US 6,060,461 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 23 is confirmed.

Claims 1, 3-9, 12, 13, 16-22, 24, 26, 27, 29-31 are determined to be patentable as amended.

Claims 2, 10, 11, 14, 15, 25, 28 dependent on an amended claim, are determined to be patentable.

New claims 32-49 are added and determined to be patentable.

1. A method for enhancing the formation of clots [on] *in* a wound of an animal where *extravascular* blood *flow* is present comprising the steps of applying porous [part] *particles having average diameter* dimensions of from about 0.5 to 1,000 micrometers to at least a portion of said wound where *extravascular* blood *flow* is present in said wound, allowing said porous particles to remain in contact with said *extravascular* blood *flow* in said wound while clotting initiates in said wound *as said porous particles allow blood liquid and low molecular weight blood components to be adsorbed onto a surface and/or absorbed into a surface of a particle.*

3. [The] *A* method [of claim 2] *for enhancing the formation of clots in a wound of an animal where extravascular blood flow is present comprising the steps of applying porous particles having average diameter dimensions of from about 0.5 to 1000 micrometers to at least a portion of said wound where extravascular blood flow is present in said wound, allowing said porous particles to remain in contact with said extravascular blood flow in said wound while clotting initiates in said wound,* wherein said porous particles have molecular sieve cutoff values between about 5,000 Daltons and 200,000 Daltons.

4. [The] *A* method [of claim 2] *for enhancing the formation of clots in a wound of an animal where extravascular blood flow is present comprising the steps of applying porous particles having average diameter dimensions of from about 0.5 to 1000 micrometers to at least a portion of said wound where extravascular blood flow is present in said wound, allowing said porous particles to remain in contact with said extravascular blood flow in said wound while clotting initiates in said wound,* wherein said *porous particles have* pores *that* comprise from 5 to 75% [b] of the volume of [the] *a* porous [particles] *particle*.

5. The method of claim [2] *4* wherein said pores comprise from 5 to 35% of the volume of the porous [particles] *particle*.

6. The method of claim 2 wherein said *porous* particles are applied to a surface of said wound with *extravascular* blood *flow* as free-flowing particles.

7. The method of claim 2 wherein said *porous* particles are applied to a surface of said wound with *extravascular* blood *flow* with said *porous* particles associated with a fabric material.

8. The [process] *method* of claim [2] *6* wherein said porous particles are applied to said [wound] surface *of said wound* along with another material selected from the group consisting of antibiotics, antifungal agents, topical pain reducing medication, pharmaceuticals, anti-inflammatants, and tissue enzyme inihibitors.

9. The [process] *method* of claim [2] *6* wherein said porous particles are applied to said [wound] surface *of said wound* on a non-human mammal along with another material selected from the group consisting of antibiotics, antifungal agents, topical pain reducing medication, animal repellant, pharmaceuticals, anti-inflammatants, and tissue enzyme inihibitors.

12. [The] *A* method [of claim 10] *for enhancing the formation of clots in a wound of an animal where extravascular blood flow is present comprising the steps of applying porous particles having average diameter dimensions of from about 0.5 to 1000 micrometers to at least a portion of said wound where extravascular blood flow is present in said wound, allowing said porous particles to remain in contact with said extravascular blood flow in said wound while clotting initiates in said wound, wherein said animal is a human, and* wherein the wound comprises broken soft tissue within a human body.

13. The method of claim 10 wherein said *porous* particles comprise a polysaccharide.

16. [The] *A* method [of claim 15] *for enhancing the formation of clots in a wound of an animal where extravascular blood flow is present comprising the steps of applying porous crosslinked polysaccharide particles having average diameter dimensions of from about 0.5 to 1000 micrometers to at least a portion of said wound where extravascular blood flow is present in said wound, allowing said porous crosslinked polysaccharide particles to remain in contact with said extravascular blood flow in said wound while clotting initiates in said wound,* wherein said animal is a human, and wherein said porous *crosslinked polysaccharide* particles have molecular sieve cutoff values between about 5,000 Daltons and 200,000 Daltons.

17. [The] *A* method [of claim 15] *for enhancing the formation of clots in a wound of an animal where extravascular blood flow is present comprisng the steps of applying porous crosslinked polysaccharide particles having average diameter dimensions of from about 0.5 to 1000 micrometers to at least a portion of said wound where extravascular blood flow is present in said wound, allowing said porous crosslinked polysaccharide particles to remain in contact with said extravascular blood flow in said wound while clotting initiates in said wound, wherein said animal is a human, and* wherein said *porous particles have* pores *that* comprise from 5 to 35% of the volume of [the] *a* porous [particles] *particle*.

18. [The] *A* method [of claim 14] *for enhancing the formation of clots in a wound of an animal where extravascular blood flow is present comprising the steps of applying porous polysaccharide particles having average diameter*

*dimensions of from about 0.5 to 1000 micrometers to at least a portion of said wound where extravascular blood flow is present in said wound, allowing said porous polysaccharide particles to remain in contact with said extravascular blood flow in said wound while clotting initiates in said wound, wherein said animal is a human,* wherein said *porous particles have* pores *that* comprise from 5 to 35% of the volume of [the] *a* porous [particles] *particle, and wherein said polysaccharide comprises dextran.*

19. The method of claim 13 wherein said *porous particles have* pores *that* comprise from 5 to 35% of the volume of [the] *a* porous [particles] *particle.*

20. The method of claim 13 wherein said *porous* particles are applied to a surface of said wound with *extravascular* blood *flow* with said *porous* particles associated with a fabric material.

21. The method of claim 1 wherein said *porous* particles comprise a polysaccharide.

22. The method of claim 1 wherein said *porous particles have a* pore size *that* is between 1 and 500 nanometers.

24. A method for enhancing the formation of clots [on] *in* a wound of an animal where *extravascular* blood *flow* is present comprising the steps of applying porous particles to *extravascular* blood *flow* in said wound without any non-clotting intermediate film or material between said *porous* particles and said *extravascular* blood *flow,* [the] *said porous* particles having average diameter dimensions of from about 0.5 to 1000 micrometers, to at least a portion of said wound where *said extravascular* blood *flow* is present, allowing said porous particles to remain in contact with said *extravascular* blood *flow in said wound* while clotting initiates in said wound *as said porous particles allow blood liquid and low molecular weight blood components to be adsorbed onto a surface and/or absorbed into a surface of a particle.*

26. The method of claim 25 wherein said *porous* particles comprise a polysaccharide.

27. The method of claim [6] *26* wherein said polysaccharide comprises dextran.

29. [The] *A* method [of claim 28] *for enhancing the formation of clots in a wound of an animal where extravascular blood flow is present comprising the steps of applying porous particles to extravascular blood flow in said wound without any non-clotting intermediate film or material between said porous particles and said extravascular blood flow, said porous particles having average diameter dimensions of from about 0.5 to 1000 micrometers, to at least a portion of said wound where said extravascular blood flow is present, allowing said porous particles to remain in contact with said extravascular blood flow while clotting initiates in said wound, wherein said animal is a mammal, and* wherein said porous particles have molecular sieve cutoff values between about 5,000 Daltons and 200,000 Daltons.

30. [The] *A* method [of claim 29] *for enhancing the formation of clots in a wound of an animal where extravascular blood flow is present comprising the steps of applying porous particles to extravascular blood flow in said wound without any non-clotting intermediate film or material between said porous particles and said extravascular blood flow, said porous particles having average diameter dimensions of from about 0.5 to 1000 micometers, to at least a portion of said wound where said extravascular blood flow is present, allowing said porous particles to remain in contact with said extravascular blood flow while clotting iniitates in said wound, wherein said animal is a mammal, wherein said porous particles have molecular sieve cutoff values between about 5,000 Daltons and 200,000 Daltons, and* wherein said *porous particles have* pores *that* comprise from 5 to 75% of the volume of [the] *a* porous [particles] *particle.*

31. The method of claim 30 wherein said pores comprise from 5 to 35% of the volume of [the] *said* porous particles.

*32. A method for enhancing the formation of clots in a wound of an animal where blood is present, the method comprising the steps of: applying porous particles having average diameter dimensions of from about 0.5 to 1000 micrometers to at least a portion of said wound where blood is present in said wound; applying pressure to said porous particles in said wound; and allowing said porous particles to remain in contact with said blood in said wound while clotting initiates in said wound.*

*33. The method of claim 32 wherein said porous particles have molecular sieve cutoff values between about 5,000 Daltons and 200,000 Daltons.*

*34. The method of claim 32 wherein said porous particles have pores that comprise from 5 to 75% of the volume of a porous particle.*

*35. The method of claim 32 wherein said wound comprises broken soft tissue within a human body.*

*36. The method of claim 32 wherein said porous particles comprise a crosslinked polysaccharide.*

*37. The method of claim 32 wherein said porous particles have a pore size that is between 1 and 500 nanometers.*

*38. The method of claim 32 wherein the step of applying pressure to said porous particles in said wound is maintained for up to about one minute.*

*39. A method for enhancing the formation of clots for an internal wound of an animal where blood is present, the method comprising: applying porous particles having average diameter dimensions of from about 0.5 to 1000 micrometers to at least a portion of said internal wound where said blood is present; and allowing said porous particles to remain in contact with said blood while clotting initiates in said internal wound.*

*40. The method of claim 39 wherein said porous particles have molecular sieve cutoff values between about 5,000 Daltons and 200,000 Daltons.*

*41. The method of claim 39 wherein said porous particles have pores that comprise from 5 to 75% of the volume of a porous particle.*

*42. The method of claim 39 wherein said porous particles comprise a crosslinked polysaccharide.*

*43. The method of claim 39 wherein said porous particles have a pore size that is between 1 and 500 nanometers.*

44. A method for enhancing the formation of clots in a wound of an animal where blood is present, the method comprising: applying porous particles having average diameter dimensions of from about 0.5 to 1000 micrometers to at least a portion of said wound where blood is present in said wound, allowing said porous particles to remain in contact with said blood in said wound while clotting initiates in said wound as said porous particles allow blood liquid and low molecular weight blood components to be adsorbed onto a microscopically porous surface and/or adsorbed into a microscopically porous surface of a porous particle that acts as a molecular sieve.

45. The method of claim 44 wherein said porous particles have molecular sieve cutoff values between about 5,000 Daltons and 200,000 Daltons.

46. The method of claim 44 wherein said porous particles have pores that comprise from 5 to 75% of the volume of a porous particle.

47. The method of claim 44 wherein said porous particles comprise a crosslinked polysaccharide.

48. The method of claim 44 wherein said microscopically porous surface have a pore size that is between 1 and 500 nanometers.

49. A method for enhancing the formation of clots for an internal wound of an animal where extravascular blood flow is present comprising the steps of:

applying porous crosslinked polysaccharide particles having average diameter dimensions of from about 0.5 to 1000 micrometers to at least a portion of said internal wound where extravascular blood flow is present in said internal wound;

applying pressure to said porous crosslinked polysaccharide particles in said internal wound; and allowing said porous crosslinked polysaccharide particles to remain in contact with said extravasclular blood flow in said internal wound while clotting initiates in said internal wound as said porous crosslinked polysaccharide particles acts as a molecular sieve by allowing blood liquid and low molecular weight blood components to be adsorbed onto a surface and/or absorbed into a surface of a porous crosslinked polysaccharide particle;

wherein said porous crosslinked polysaccharide particles have molecular sieve cutoff values between about 5,000 Daltons and 200,000 Daltons;

wherein said porous crosslinked polysaccharide particles have pores that comprise from 5 to 75% of the volume of a porous crosslinked polysaccharide particle; and wherein said porous crosslinked polysaccharide particles have a pore size that is between 1 and 500 nanometers.

\* \* \* \* \*